US009675743B2

(12) United States Patent
Raiford et al.

(10) Patent No.: US 9,675,743 B2
(45) Date of Patent: Jun. 13, 2017

(54) METHODS OF MAKING MEDICAL SOLUTIONS AND RELATED SYSTEMS

(71) Applicant: Fresenius Medical Care Holdings, Inc., Waltham, MA (US)

(72) Inventors: Wayne Ronald Raiford, Vallejo, CA (US); Sue-Jane Lee, Fremont, CA (US); Martin Joseph Crnkovich, Walnut Creek, CA (US); Robert E. Hassard, Benicia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 13/630,123

(22) Filed: Sep. 28, 2012

(65) Prior Publication Data
US 2014/0091022 A1    Apr. 3, 2014

(51) Int. Cl.
| | | |
|---|---|---|
| B01D 35/00 | (2006.01) |
| C02F 1/68 | (2006.01) |
| B01F 13/00 | (2006.01) |
| A61M 1/16 | (2006.01) |
| B01F 5/04 | (2006.01) |
| B01F 15/00 | (2006.01) |
| B01F 1/00 | (2006.01) |

(52) U.S. Cl.
CPC ........ *A61M 1/1656* (2013.01); *A61M 1/1666* (2014.02); *B01F 1/0027* (2013.01); *B01F 1/0038* (2013.01); *B01F 5/0496* (2013.01); *B01F 15/0035* (2013.01); *B01F 15/00136* (2013.01); *B01F 15/00194* (2013.01); *A61M 2205/3331* (2013.01); *A61M 2205/3379* (2013.01); *A61M 2205/3393* (2013.01)

(58) Field of Classification Search
None
See application file for complete search history.

(56) References Cited

U.S. PATENT DOCUMENTS

| | | | | |
|---|---|---|---|---|
| 3,762,557 | A | * | 10/1973 | Tudor et al. ............... 210/242.3 |
| 4,618,343 | A | * | 10/1986 | Polaschegg .................... 604/29 |
| 4,718,447 | A | | 1/1988 | Marshall |

(Continued)

FOREIGN PATENT DOCUMENTS

| | | |
|---|---|---|
| WO | WO9937342 A1 | 7/1999 |
| WO | WO0249968 A2 | 6/2002 |

(Continued)

OTHER PUBLICATIONS

International Search Report and Written Opinion for corresponding PCT Application No. PCT/US2013/061928, mailed Dec. 2, 2013, 14 pages.

(Continued)

*Primary Examiner* — Richard Gurtowski
(74) *Attorney, Agent, or Firm* — Fish & Richardson P.C.

(57) ABSTRACT

This disclosure relates to making medical solutions. In certain aspects, a method is performed by a data processing apparatus. The method includes introducing liquid into a container that contains a dissolvable solid concentrate in a manner so that a layer of solution above the solid concentrate is maintained at a depth that allows the liquid introduced into the container to agitate the solution adjacent to the solid concentrate to cause mixing of the solid concentrate with the solution.

21 Claims, 5 Drawing Sheets

(56) References Cited

U.S. PATENT DOCUMENTS

| | | | | |
|---|---|---|---|---|
| 4,812,239 A * | 3/1989 | Mills | ............... | A61M 1/1656 210/647 |
| 5,015,389 A * | 5/1991 | Portillo, Jr. | ......... | A61M 1/1656 210/646 |
| 5,141,493 A * | 8/1992 | Jacobsen et al. | ............... | 604/29 |
| 5,811,581 A * | 9/1998 | Piva | ............... | B01D 61/027 210/635 |
| 2005/0201200 A1* | 9/2005 | Fleig | ............... | B01F 1/0022 366/153.1 |

FOREIGN PATENT DOCUMENTS

| | | |
|---|---|---|
| WO | WO2004089441 A1 | 10/2004 |
| WO | WO2011066299 A1 | 6/2011 |
| WO | WO2012041790 A1 | 4/2012 |

OTHER PUBLICATIONS

Notification Concerning Transmittal of International Preliminary Report on Patentability for corresponding PCT Application No. PCT/US2013/061928, mailed Apr. 9, 2015, 10 pages.
Communication from European Patent Office from European Application No. 13 780 435.7, mailed Feb. 1, 2016, 8 pages.

* cited by examiner

METHODS OF MAKING MEDICAL SOLUTIONS AND RELATED SYSTEMS

TECHNICAL FIELD

This invention relates to methods of making medical solutions and related systems.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

The dialysis solutions or dialysates used during hemodialysis typically contain sodium chloride and other electrolytes, such as calcium chloride, or potassium chloride, a buffer substance, such as bicarbonate, or acetate and acid to establish a physiological pH, plus optionally, glucose or another osmotic agent.

SUMMARY

In one aspect of the invention a method is performed by a data processing apparatus. The method includes introducing liquid into a container that contains a dissolvable solid concentrate in a manner so that a layer of solution above the solid concentrate is maintained at a depth that allows the liquid introduced into the container to agitate the solution adjacent to the solid concentrate to cause mixing of the solid concentrate with the solution.

In another aspect of the invention a dialysis system includes a container containing a dissolvable solid concentrate, an input line connected to the container and to a valve that controls the flow of liquid into the container, an output line connected to the container and to a pump, and a data processing apparatus connected to the valve and configured for introducing liquid into the container through the line in a manner so that a layer of solution above the solid concentrate is maintained at a depth that allows the liquid introduced into the container to agitate the solution adjacent to the solid concentrate to cause mixing of the solid concentrate with the solution.

Implementations can include one or more of the following features.

In certain implementations, the solid concentrate is a salt.

In certain implementations, the salt is sodium bicarbonate.

In certain implementations, the method includes obtaining a measurement of a volume of solution pumped from the container by a pump during a first period of time, and determining a second period of time based on the measurement.

In certain implementations, introducing the liquid comprises opening a valve that controls the flow of the liquid into the container for the second period of time.

In certain implementations, the first period of time is based on a number of cycles of a balance chamber connected to the pump.

In certain implementations, the method includes pumping the solution to a dialyzer.

In certain implementations, the depth of the layer of solution is 0.5 to 1.5 inch.

In certain implementations, the method includes obtaining a measurement of pressure within the container, comparing the measurement to an expected pressure, and determining a period of time based on the comparison;

In certain implementations, introducing the liquid includes opening a valve that controls the flow of the liquid into the container for the period of time.

In certain implementations, the method includes obtaining a measurement of the weight of the container, comparing the measurement to an expected weight, and determining a period of time based on the comparison.

Implementations can include one or more of the following advantages.

In some implementations, the methods described provide improved utilization of a solid concentrate (e.g., a powdered sodium bicarbonate concentrate) in a dialysis system. Using conventional methods, excess liquid is often times added to a medical solution container (e.g., a sodium bicarbonate solution container) during dialysis to reduce the likelihood of pumping air from the container as the container is emptied during treatment. As a result, a thick layer of solution (e.g., sodium bicarbonate solution) tends to form over the solid concentrate at the bottom of the container. The thick layer of solution dissipates the force of additional liquid being added to the container, and thereby limits agitation of the solution near its interface with the solid concentrate. This can decrease dissolution of the solid concentrate into the solution and can thus prevent the solution from becoming saturated. The inventors have found that by limiting the layer of liquid or solution covering the layer of solid concentrate to 0.5 to 1.5 inch, the force of new liquid being added to (e.g., dropped into) the container is sufficient to agitate the solid concentrate and thus promote dissolution of the solid concentrate within the added liquid. At the same time, the layer of liquid or solution is sufficiently thick to prevent air from being pumped from the container as the container is emptied during treatment. In this manner, more of the solid concentrate is dissolved into the liquid, less of the solid concentrate is wasted, and the duration of the dialysis treatment without intervention is increased.

In addition to the benefits discussed above, maintaining a thinner layer of liquid or solution over the layer of solid concentrate at the bottom of the container can reduce the amount of time required to empty the container after completion of a treatment. As a result, the total amount of time required by the clinician to complete post-treatment procedures can be reduced such that more of the clinician's time can be spent caring for patients.

DETAILED DESCRIPTION

In general, the invention relates to methods of making medical solutions and related systems. In some aspects of the invention, a dialysis system (e.g., a hemodialysis system) includes a controller that controls the dialysis system to carry out a dialysis treatment. The controller receives signals from a pump that pumps a medical solution (e.g., a sodium bicarbonate solution) from a container, such as a bag, into a feeder line. By monitoring the volume of solution pumped from the container, the controller can determine a volume of liquid to add to the container to maintain a liquid level in the container that facilitates the dissolution of a solid concentrate (e.g., a powdered sodium bicarbonate concentrate) into the liquid or solution. The solution above the solid concentrate can, for example, have a depth that is maintained within a desired range to ensure that the introduction of additional liquid into the container will agitate the portion of the solution adjacent the solid concentrate and cause the solid concentrate to mix with the solution.

Figure 1:
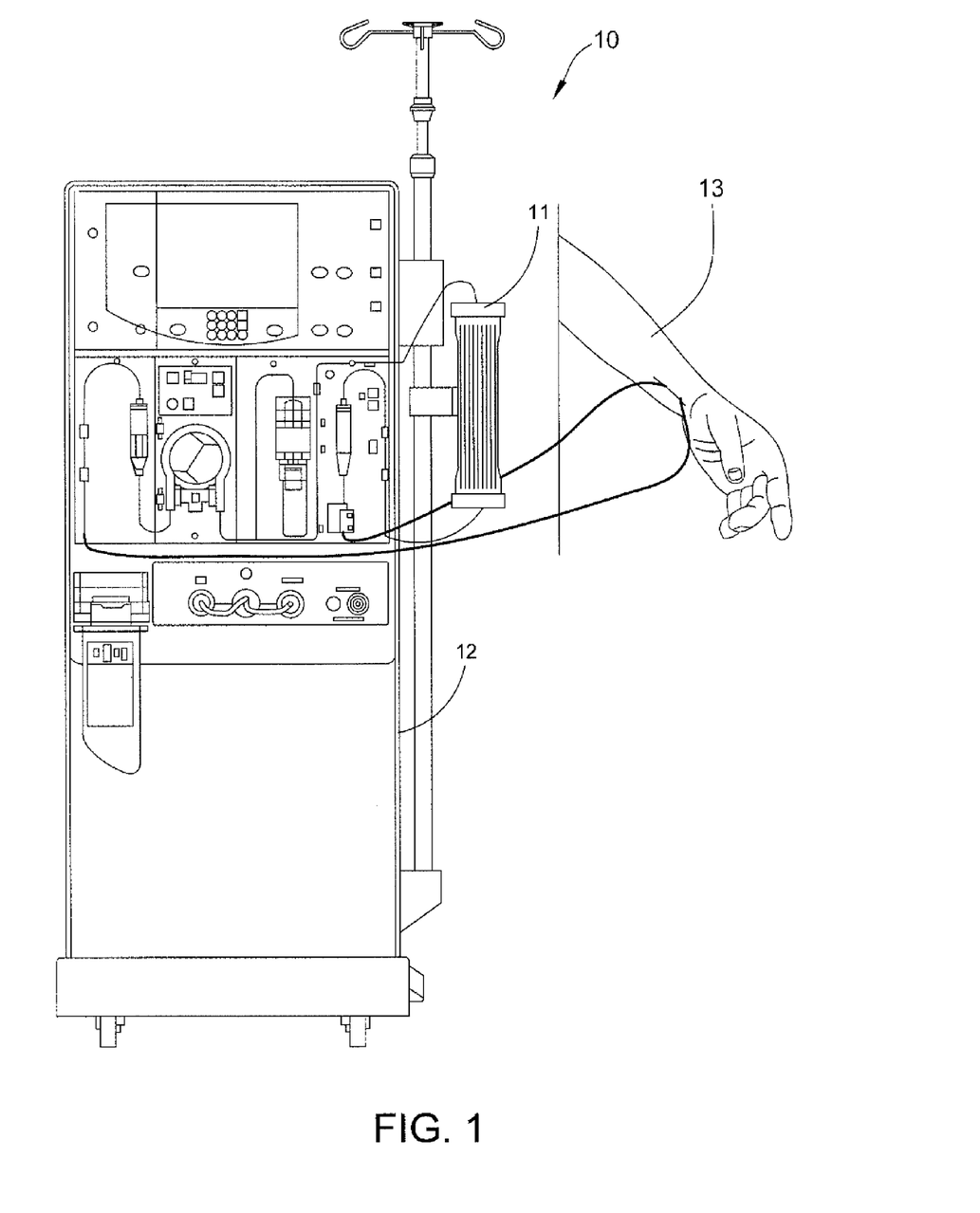
FIG. 1 is a schematic diagram of a hemodialysis system that is connected to a patient.

Referring to FIG. 1, a dialysis system 10 includes a dialysis machine 12 that includes a subsystem 15 for preparing a sodium bicarbonate solution from a powdered sodium bicarbonate concentrate to form dialysate. During treatment a disposable fluid line set and a dialyzer 11 is connected to the machine 12 and to a patient 13 to permit the patient's blood to circulate through the fluid line set and dialyzer 11. Fluid lines also extend from the machine 12 to the dialyzer 11 to allow the dialysate to pass through the dialyzer 11 with the blood. As the blood and dialysate pass through the dialyzer 11, toxins move across a semi-permeable surface of the dialyzer 11 from the blood to the dialysate.

Figure 2:
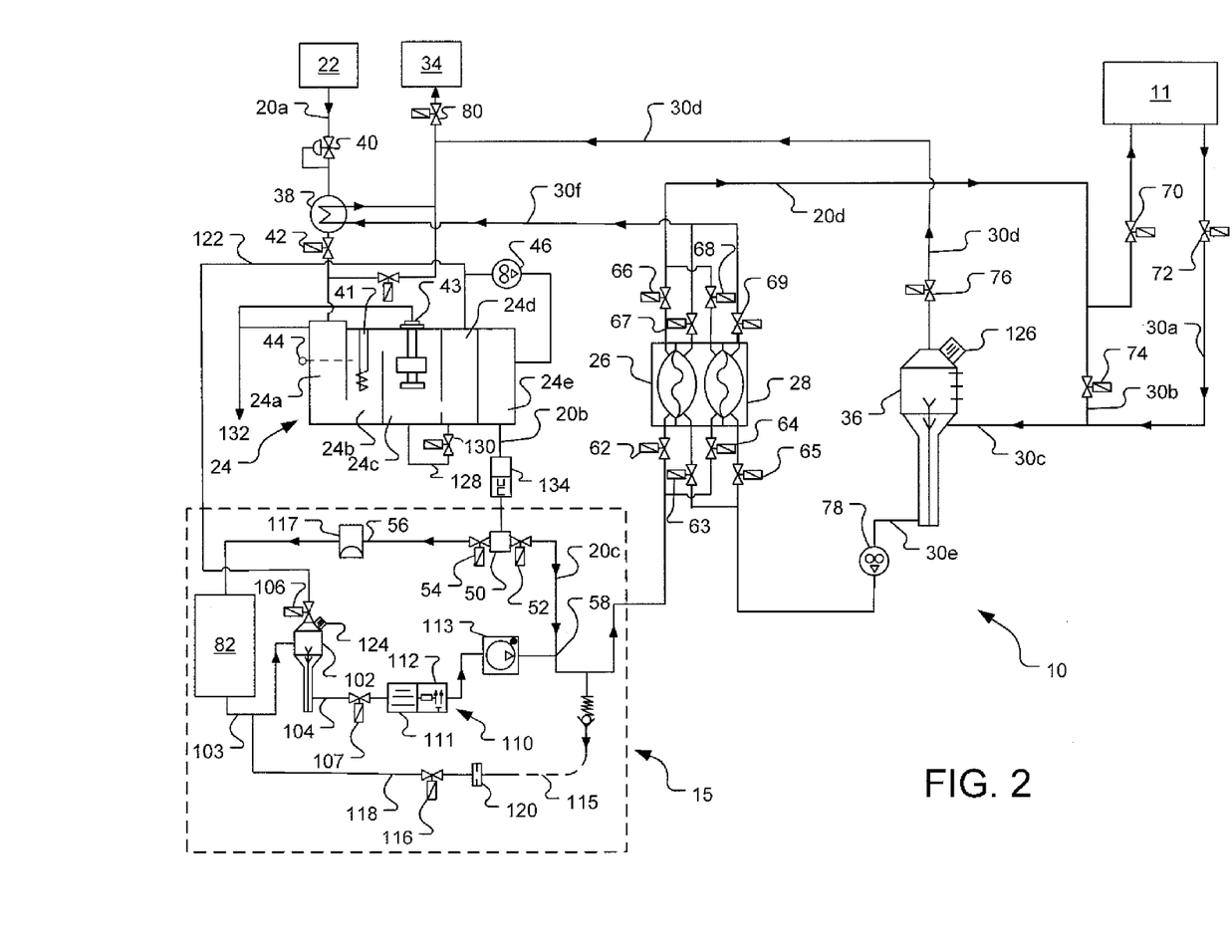
FIG. 2 is a schematic diagram of a dialysate circuit and associated components of the hemodialysis system of FIG. 1.

FIG. 2 illustrates a representative hydraulic arrangement of the dialysis system 10. Many of the illustrated components are housed inside the machine 12 and are thus not visible in FIG. 1. By way of a general overview of the operation, the system 10 includes main fluid line segments 20a-d (collectively referred to as a mainline 20) that are fluidly coupled to a fluid source 22 at one end, and to the dialyzer 11 at the other end, with various optional assemblies disposed along the mainline 20. In some implementations, optional assemblies are disposed along the mainline 20 for preparing the sodium bicarbonate solution or dialysate and may include a hydroblock 24 and one or more balancing chambers 26, 28.

Line segments 30a-f (collectively referred to as a return line 30) from the dialyzer 11 provides return flow from the dialyzer 11 to a drain 34. Subassemblies such as an air separation chamber 36 and a heat exchanger 38 are provided along the return line 30. It is noted that not all elements of the illustrated hydraulic arrangement are necessary to the structure and operation of the subsystem 15 for preparing a sodium bicarbonate solution from a powdered sodium bicarbonate concentrate, although a general explanation is provided herein in the interest of completeness.

Turning now to the specifics of the illustrated hydraulic arrangement, the fluid source 22 includes any appropriate type of liquid or liquids, such as a reverse osmosis water (RO water) source. Liquid from the fluid source 22 flows through the mainline segment 20a to the hydroblock 24. In some implementations, the heat exchanger 38, a pressure regulator 40, and a control valve 42 are provided along the mainline segment 20a between the fluid source 22 and the hydroblock 24. The heat exchanger 38 heats the liquid somewhat with heat from the return spent dialysate, as will be discussed below.

The hydroblock 24 is a multichambered unit (chambers 24a-24e being illustrated). The liquid is heated by a heater 41 in chamber 24b and vented to a vent 43 in chamber 24c as the liquid flows through the various chambers 24a-e of the hydroblock 24. The liquid temperature within the hydroblock 24 is monitored and/or controlled by a control thermostat 44. A deaeration pump 46 pumps liquid between the fourth and fifth chambers 24d, 24e of the hydroblock 24 to return the liquid to the mainline segment 20b.

Leaving the hydroblock 24, the mainline segment 20b bifurcates at a branch point 50. Valves 52, 54 control the flow of liquid to the continuing mainline segment 20c and a subsystem line 56, respectively. If the valve 54 is closed and the valve 52 is open, the liquid continues through the valve 52 to the mainline segment 20c. Conversely, if the valve 54 is open and the valve 52 is closed, liquid proceeds through the valve 54 to the subsystem line 56. As with all of the valves in this disclosure, the valves 52, 54 may be simple shut-off valves, or other multiposition valves. In alternative embodiments, the valves 52, 54 are replaced by a single valve that includes positions that arrest flow entirely, that direct flow to the subsystem line 56, or that direct flow along the mainline segment 20c.

The subsystem line 56 connects flow from the mainline segment 20b to the subsystem 15 for preparing a sodium bicarbonate solution, as will be explained in greater detail below. After leaving the subsystem 15, the sodium bicarbonate solution is returned to the mainline segment 20c at junction 58. The continuing mainline segment 20c directs flow to the balance chambers 26, 28. Flow through the balancing chambers 26, 28 is controlled by valves 62-69. Each of the balancing chambers 26, 28 includes two separate subchambers separated by a flexible membrane, the significance of which will be discussed below. Flow from the subsystem 15 flows into the respective balancing chambers 26, 28 through valves 62 and 64, and out from the balancing chambers 26, 28 through valves 66, 68. Valves 63, 65, 67, and 69 control flow of spent dialysate, as further described below.

Leaving the balancing chambers 26, 28, the solution is directed through mainline segment 20d. Flow to and from the dialyzer 11 is controlled by a pair of control valves 70, 72 disposed along the mainline segment 20d and the return line segment 30a, respectively, as well as a bypass valve 74 disposed in bypass line 30b between the mainline segment 20d and the return line segment 30a. Thus, dialysate from the balancing chambers 26, 28 flowing through mainline segment 20d moves on to the dialyzer 11 when dialyzer inlet valve 70 is in the open configuration and bypass valve 74 in the bypass line 30b is in the closed position.

As the dialysate flows through the dialyzer 11 so does a patient's blood. As a result, toxins, such as urea, are transferred across a semi-permeable structure (e.g., semi-permeable microtubes) of the dialyzer 11 from the patient's blood to the dialysate.

Following the dialyzer 11, spent dialysate passes the control valve 72 to return to the machine 12 through return line segments 30a and 30c with the bypass valve 74 in the closed position. To ensure accurate operation of the balancing chambers 26, 28, as discussed below, spent dialysate passes into the air separation chamber 36 before reaching the balance chambers 26 and 28. From the air separation chamber 36, separated gases, and potentially fluid, are passed through return line segment 30d to the drain 34 by opening shutoff valves 76 and 80. Return dialysate, from which the gases have been separated in the air separation chamber 36, may be pumped by flow pump 78 through return line segment 30e to one or both of the balance chambers 26, 28 through valves 63, 65. Leaving the balance chambers 26, 28 through valves 67, 69, respectively, the spent dialysate is directed to a heat exchanger 38 and the drain 34 by way of return line segment 30f. Overall flow to the drain 34 is controlled by shutoff valve 80.

Within the balance chambers 26, 28, fresh dialysate from the subsystem 15 passes along one side of the internal membranes, while spent dialysate passes along the other side of the internal membranes. Pumping of spent dialysate from line segment 30e along one side of the membrane with fresh dialysate passing along the other side of the membrane from mainline segment 20c results in a balanced provision of dialysate from and to the dialyzer 11 during use.

The structure and operation of the subsystem 15 for preparation of the sodium bicarbonate solution will now be explained. Still referring to FIG. 2, liquid flowing through the mainline segment 20b from the hydroblock 24 is directed to the subsystem 15 by opening the control valve 54 and closing the control valve 52 at adjacent junction 50 to provide flow to the subsystem line 56. To prepare the sodium bicarbonate solution, liquid from the subsystem line 56 enters a bag 82, which contains a powdered sodium bicarbonate concentrate. During the filling process, the valve 54 periodically closes allowing a pressure sensor 117 to read the pressure within the bag 82. The bag can be filled until a threshold pressure is reached. The threshold pressure is typically about 150 mmHg During treatment the pressure is about 90 mmHg at the start of the treatment and about 20 mmHg at the end of the treatment. In some implementations, the threshold pressure is 90 mmHg. The liquid fills the bag and saturates the dry form sodium bicarbonate concentrate that sits at the bottom of the bag 82. The bag 82 can, for example, be a collapsible, replaceable bag that encloses the powdered sodium bicarbonate concentrate.

Figure 3:
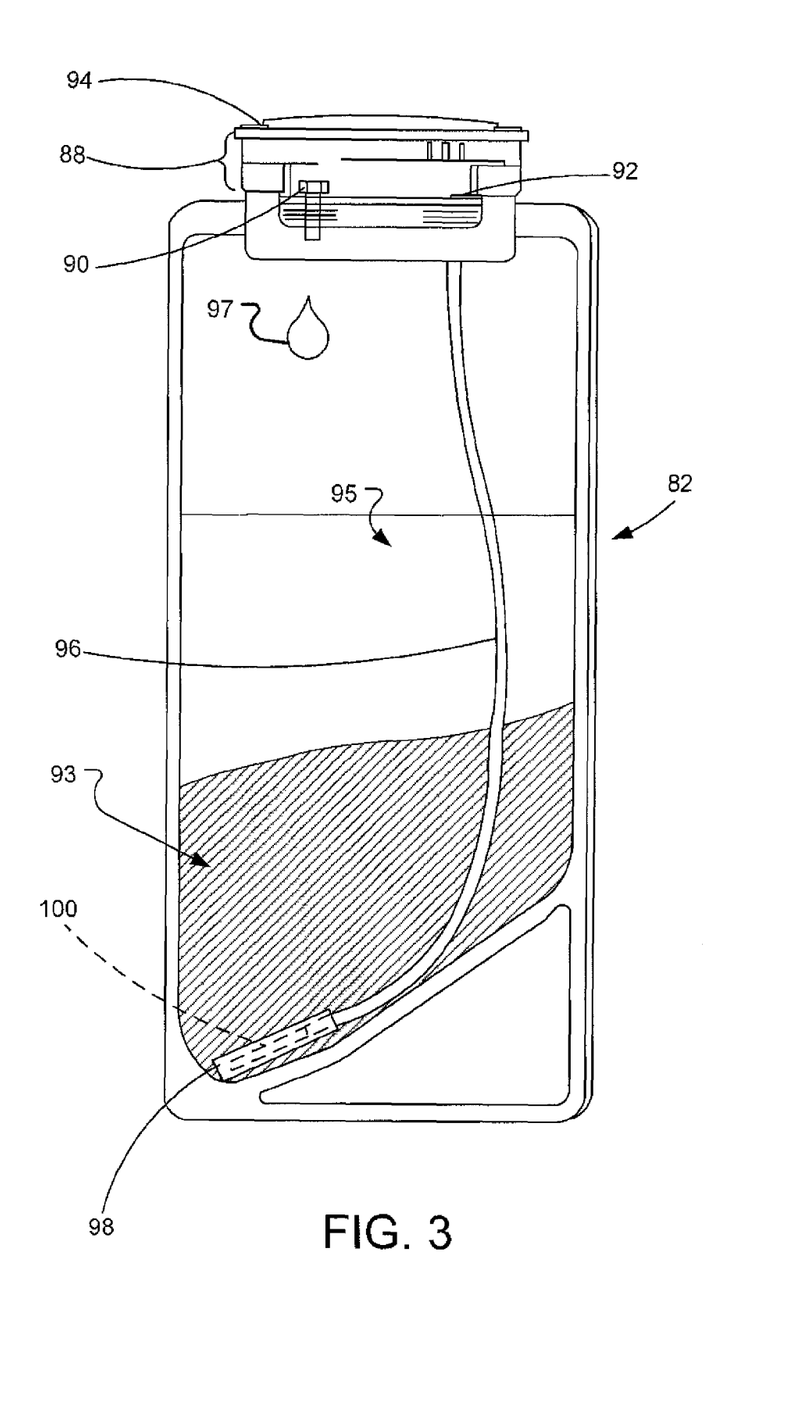
FIG. 3 is a representative partially cross-sectioned view of a collapsible bag of the hemodialysis system of FIG. 1 that contains a powdered sodium bicarbonate concentrate.

An example of a suitable bag 82 is shown in FIG. 3. In this partially cross-sectioned view, the bag 82 includes a protective cover 94. In some implementations, the bag 82 is coupled to the subsystem 15 by a connector 88 having an inlet 90 and an outlet 92. Although the inlet 90 and outlet 92 are shown in an upper portion of the bag 82, the inlet 90 and outlet 92 may be disposed elsewhere, so long as the requisite mixing is obtained. For example, the inlet may be disposed in a lower portion of the bag 82 to allow the liquid to be injected upward into the bag 82 to encourage agitation to facilitate mixing.

In order to allow the mixed sodium bicarbonate solution to be withdrawn from the bag 82 when it is not completely full, the outlet 92 originates below the level of liquid in the bag 82. In some implementations, a tube 96 having a lower opening 98 is fluidly coupled to the outlet 92 such that the opening 98 is disposed in a lower portion of the bag 82, that is, below the liquid level. The tube 96 sits atop a layer of powdered sodium bicarbonate concentrate 93 at the bottom of the bag 82. To inhibit the intake of powdered sodium bicarbonate that is not yet dissolved, a filter 100 is disposed at the opening 98. The filter 100 can be made of any appropriate material, such as porous polyethylene. The bag 82 and connector 88 are typically made of high density polyethylene, but other suitable materials can be used.

Carbon dioxide will typically be generated from the initial contact between the liquid and the sodium bicarbonate powder. Residual air is also often disposed within the bag 82. As explained above, in order to provide proper removal of the sodium bicarbonate solution from the bag 82, the opening 98 into the outlet 92 of the bag 82 is maintained below the surface of the liquid contained therein. It will thus be appreciated that a reduction of gases disposed within the bag 82 typically provides more space for the introduction of liquid.

In general, during operation the bag 82 includes a layer of sodium bicarbonate solution 95 over the layer of powdered sodium bicarbonate concentrate 93 because the powdered sodium bicarbonate is denser than the solution and rests on the bottom of the bag 82. As liquid 97 is added to the bag 82 through inlet 90, the liquid 97 falls into the layer of solution 95 causing agitation in the portion of the solution directly adjacent the layer of undissolved sodium bicarbonate powder and thereby causing the sodium bicarbonate powder to become mixed with the solution. This mixing action assists in the dissolution of the sodium bicarbonate powder into the solution, and thus helps to ensure that the solution becomes saturated.

If the layer of solution 95 is too shallow (e.g., less than 0.5 inch above the layer of sodium bicarbonate 93), then there may be insufficient liquid to dissolve the dry form sodium bicarbonate. If the layer of solution 95 is too deep (e.g., greater than 1.5 inch above the layer of sodium bicarbonate 93), then the layer of liquid 95 will dampen the added liquid 97 and there may not be sufficient agitation between the liquid and the dry form sodium bicarbonate to adequately mix the sodium bicarbonate with the solution. As discussed below, in some implementations, the system 10 is configured to maintain the layer of solution 95 at a thickness (or depth) of 0.5 inch to 1.5 inch above the layer of sodium bicarbonate powder 93 to help ensure that adequate mixing of the sodium bicarbonate powder 93 with the solution 95 occurs as supplemental liquid 97 is introduced into the bag 92.

Returning to FIG. 2, in order to expel air from the subsystem 15, an air separation chamber 102 is provided downstream of the bag 82. The air separation chamber 102, which is fluidly connected to the bag 82 by a subsystem line 103, is designed to remove both air residually disposed within the bag 82 and gases precipitating out of the bicarbonate solution during operation of the subsystem 15. During operation, air rises to the top of the air separation chamber 102, while the bicarbonate solution settles to the bottom of the air separation chamber 102. In use, bicarbonate solution is passed from the air separation chamber 102 to subsystem line 104, while gases are passed from the air separation chamber 102 by operation of valve 106.

Turning first to the passage of bicarbonate solution from the air separation chamber 102, flow through the subsystem line 104 is controlled by operation of a valve 107. When valve 107 is in the open position and valve 106 is in the closed position, bicarbonate solution flows through subsystem line 104 to a conductivity detector 110 that includes a conductivity cell 111 and a temperature detector 112. In some implementations, the temperature detector 112 is a thermister, which is a resistor in which the resistance varies significantly with temperature. The conductivity cell 111 measures the conductivity of or provides a representative reading of the bicarbonate level of solution leaving the air separation chamber 102. From the conductivity cell 111 and temperature detector 112, a bicarbonate pump 113 pumps the bicarbonate solution to rejoin the mainline segment 20c at junction 58, via which the bicarbonate solution is passed to one or both of the balancing chambers 26, 28, and on to the dialyzer 11.

During normal operation, the air separation chamber 102 separates gas from the bicarbonate solution or dialysate progressing to the junction 58 for delivery to the dialyzer 11, while the air separation chamber 36 separates gas from spent dialysate returning from the dialyzer 11. It will be appreciated that this elimination of the gases in the dialysate flowing to and from the dialyzer 11 facilitates efficient and accurate operation of the balancing chambers 26, 28 during regular operation of the system 10.

In order to determine if and when gas has accumulated in the air separation chamber 102, an air sensor 124 is provided in the air separation chamber 102. In some implementations, the air sensor 124 is a two-pronged air detection probe located at the top of the air separation chamber 102 such that an electric current between the two prongs is detected when liquid fills the chamber 102 to at least the level of the prongs. Conversely, when there is air in the chamber 102, the air between the two prongs acts as an insulator and electric current does not flow. A similar air sensor 126 is provided in air separation chamber 36 to provide an indication of when valve 76 should be opened to allow passage of gases from air separation chamber 36 to return line segment 30d.

Flow through the air separation chamber 102 is controlled by the control valve 106. If air is not detected in the air separation chamber 102, the control valve 106 is closed, and the solution proceeds through subsystem line 104, advanced by the pump 113 to rejoin the mainline segment 20c at junction 58. The solution is then passed on to the balance chambers 26, 28 and to the mainline segment 20d for delivery to the dialyzer 11, as explained above.

Conversely, if the air sensor 124 detects air in the air separation chamber 102, the control valve 106 is opened to vent gases from the air separation chamber 102 to degassing line 122. The degassing line 122 provides a fluid connection to the hydrochamber 24 such that gases accumulated in the air separation chamber 102 are passed to the hydrochamber 24. The degassing line 122 is connected to the third chamber 24c of the hydrochamber 24. In use, only gases typically are released from the separation chamber 102 through the valve 106 for very short periods of time, rather than an air/sodium bicarbonate solution combination.

Some implementations further include a bypass line 128 in which a valve 130 is disposed, coupling the degassing line 122 to the fourth chamber 24d. During cleaning modes of the machine, the valve 130 is opened in order to relieve pressure built up within the hydrochamber 24.

To assist in the separation of gases from the fluid contained within the hydrochamber 24, the third chamber 24c of the hydrochamber 24 includes a venting structure 43. Gases entering the third chamber 24c from the degassing line 122 rise upward through the fluid contained within the hydrochamber 24 to the upper portion of the third chamber 24c to be vented through the venting structure 43 to a drain or the atmosphere 132.

Under normal operation, only gases are typically vented from the air separation chamber 102 through the degassing line 122 to the hydrochamber 24. In order to ensure that the valve 106 and air sensor 124 are operating properly, that is, in order to monitor whether any of the sodium bicarbonate solution is being vented from the air separation chamber 102 to the hydrochamber 24 through the degassing line 122, a conductivity sensor 134 is provided between the hydrochamber 24 and the bag 82. In this way, a direct conductivity number is determined for the fluid as it flows from the hydrochamber 24 to the mainline segment 20c or subsystem line 56.

The measured conductivity number is compared to a reference conductivity number for fluid that is not diluted with a sodium bicarbonate solution. If the measured conductivity number differs from the reference conductivity by greater than a given amount or percentage, or if the measured conductivity number does not fall within a predetermined reference range, then further corrective action is taken. Further corrective action may include, by way of example, shutting down the system 10 or providing a warning light or the like that the subsystem 15, the air separation chamber 102, the valve 106, and/or the sensor 124 must be checked.

The conductivity sensor 134 is also utilized to supply a measured conductivity number to a controller with regard to the liquid conductivity, as opposed to an estimated conductivity number, which is often utilized in calculations related to operation of dialysis systems. For example, such systems often assume that the liquid, e.g., water, has no conductivity. The measured conductivity number provided by the conductivity sensor 134 for liquid leaving the hydrochamber 24 is utilized in system calculations as opposed to an assumed or estimated conductivity number. As a result, a more accurate conductivity number can be used.

The system 10 may include one or more controllers (not illustrated), which are capable of receiving signals from and activating one or more of the pumps 46, 78, 113 and one or more of the valves 42, 52, 54, 62-70, 72, 74, 76, 80, 106, 107, 116, 130, and receiving input from air sensors 124, 126, and conductivity detector 110, conductivity cell 111, temperature detector 112, and conductivity sensor 134. For example, in some implementations, a Microchip PIC18F6410 (manufactured by Microchip Technology, Inc. (Chandler, Ariz.)) is used for the controller.

During treatment, liquid, typically purified water, is delivered from the hydrochamber 24 to the bag 82. The water mixes with the sodium bicarbonate powder in the bag 82 to produce the sodium bicarbonate solution used as the dialysate. While the sodium bicarbonate solution is described as being used as the dialysate in this system, it should be understood that one or more additional additives can also be added to the sodium bicarbonate solution to form the dialysate. The dialysate is delivered to the dialyzer 11 via the balancing chambers 26, 28, which ensure that the volume of dialysate delivered to the dialyzer 11 is approximately equal to the volume of spent dialysate exiting the dialyzer 11. The dialysate passes through the dialyzer 11 along with a patient's blood to filter the blood and remove toxins from the blood. The spent dialysate containing the removed toxins is then sent to the drain 34 via the balancing chambers 26, 28.

Figure 4:
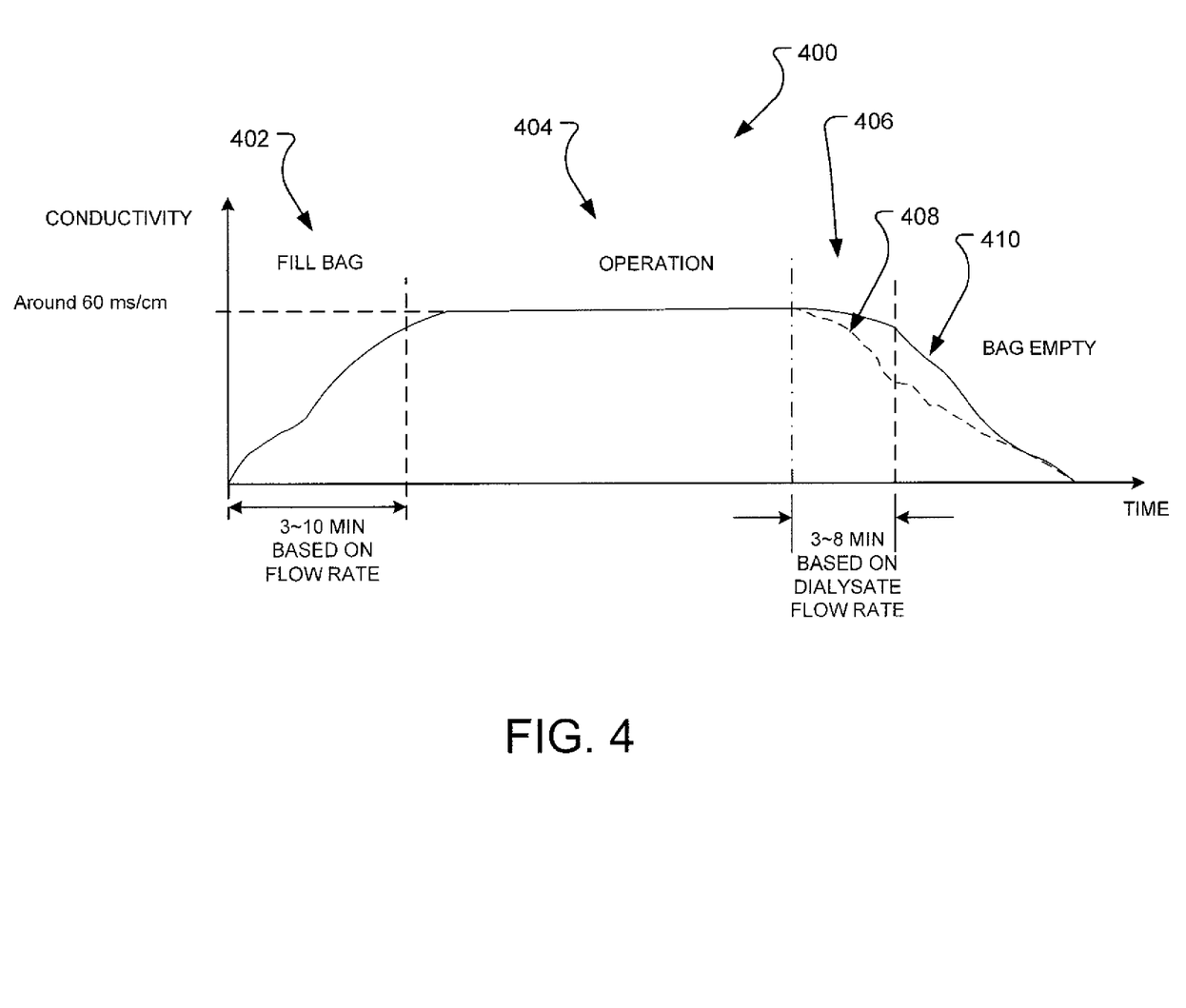
FIG. 4 is a graph depicting the conductivity of a sodium bicarbonate solution flowing from the collapsible bag of the hemodialysis system of FIG. 1 during a dialysis treatment.

FIG. 4 illustrates an example conductivity level of the sodium bicarbonate solution during operation of the machine. The conductivity level of the solution when the layer of solution 95 is maintained at a thickness of 0.5 inch to 1.5 inch above the sodium bicarbonate powder layer 93 in the bag 82 is shown by solid line 410 in FIG. 4, while the dashed line 408 shows the conductivity level of solution that typically results in systems that allow thicker layers of solution to accumulate over the sodium bicarbonate powder layer.

Still referring to FIG. 4, at the beginning portion 402 of the operation, the bag 82 is being filled with purified water to produce the dialysate. During this beginning portion 402, the conductivity of the bicarbonate solution rises, for example, from 0 mS/cm to about 60 mS/cm. The beginning portion 402 lasts, for example, about three to ten minutes, depending on the flow rate of the purified water into the bag 82. During the beginning portion 402, the bag continues to fill and the operation of the valve 54 is not affected by the operation of the bicarbonate pump 113. As the bag 82 fills, the pressure within the bag also increases. The liquid typically continues to be introduced into the bag 82 until the pressure within the bag 82 reaches a predetermined level (e.g., 90 mmHg).

During the middle portion 404 of the operation of the machine, the dialysate is passed through the dialyzer 11 along with blood of the patient to perform the dialysis treatment. The conductivity of the bicarbonate solution remains at a relatively high and steady level (e.g., around 60 mS/cm) during this middle portion 404. The relatively high and steady level lasts for the majority of the operation of the machine. During the middle portion 404, the volume of liquid added to the bag is approximately equal to the volume of liquid pumped by the bicarbonate pump 113, as discussed below.

As the solid bicarbonate is depleted, the solution becomes more diluted towards the end portion 406 of the operation. Accordingly, the conductivity of the solution decreases, for example, to 0 mS/cm, as the solution increases in ratio of liquid to bicarbonate. During the end portion 406, the volume of liquid added to the bag is approximately equal to the volume of liquid pumped by the bicarbonate pump 113. The pressure sensor 117 may be used to monitor the pressure in the bag and ensure that the pressure in the bag does not drop below 20 mmHg. As evident from comparing the trajectory of the dashed line 408, which represents the conductivity of bicarbonate solution over time using a conventional system that does not maintain a 0.5 inch to 1.5 inch layer of liquid above the sodium bicarbonate, to the trajectory of the solid line 410, which represents the conductivity of bicarbonate solution over time while maintaining a 0.5 inch to 1.5 inch layer of liquid above the sodium bicarbonate, the concentration of the sodium bicarbonate solution can be increased (comparatively) during the end portion 406 of the operation of the machine by providing continued agitation of the sodium bicarbonate solution in the bag, which results from the thinner layer of solution over the sodium bicarbonate powder. conductivityconductivityconductivityconductivity The increased conductivityconductivityconductivity is the result of increased levels of sodium bicarbonate in the solution. Increasing the levels of sodium bicarbonate in the solution can increase the useful life of the solid bicarbonate.

Referring again to FIG. 2, as discussed above, the bicarbonate pump 113 pumps sodium bicarbonate solution from the bag 82 and air separation chamber 102 into the mainline segment 20c. The bicarbonate pump 113 measures the volume of sodium bicarbonate solution pumped into the mainline segment 23. The bicarbonate pump 113 reports the volume of sodium bicarbonate solution to a controller (not shown).

Periodically, for example, once every two strokes of the balancing chambers 26, 28, the controller determines how long to open the valve 54 in order to replenish the volume of liquid into the bag. The controller may determine a period of time to open the valve 54 based on the reported volume of bicarbonate solution pumped from the bag 82 and the known characteristics of the valve 54. For example, if opening the valve may allow the passage of 1 ml of liquid through the valve per second and the bicarbonate pump 113 reports that a volume of 3 ml has been pumped from the bag 82, then the controller determines to open the valve 54 for 3 seconds.

The amount of time that the value is opened is proportional to the amount of liquid to be added to the bag 82. For example, the amount of liquid passing through a specific type of valve in a given period of time can be determined using a look-up table of the type shown below. Of course, it should be understood that different valves may have different performance characteristics.

| Time (ms) | Volume (ml) |
| --- | --- |
| 50 | 1.86 |
| 40 | 1.52 |
| 30 | 1.18 |
| 20 | 0.84 |
| 10 | 0.3 |

The controller opens the valve 54 to allow liquid into the bag 82 for the determined time. As a result the controller maintains the layer of liquid over the layer of dry form sodium bicarbonate to the appropriate depth as described above.

During the operation of the dialysis machine, as the bag 82 empties, the pressure detected by the pressure sensor 117 decreases. For example, the pressure may decrease from 90 mmg to 60-70 mmg Generally the pressure will not be permitted to drop below 20 mmg as this indicates that the level of liquid in the bag 82 has dropped below an acceptable level.

If the level of the liquid in the bag 82 becomes too low, several consecutive air vents can occur in the air separation chamber 102. In response to the repeated air vents, the controller may open the valve 54 to allow liquid to enter the bag 82 independent of the bicarbonate pump 113.

Figure 5:
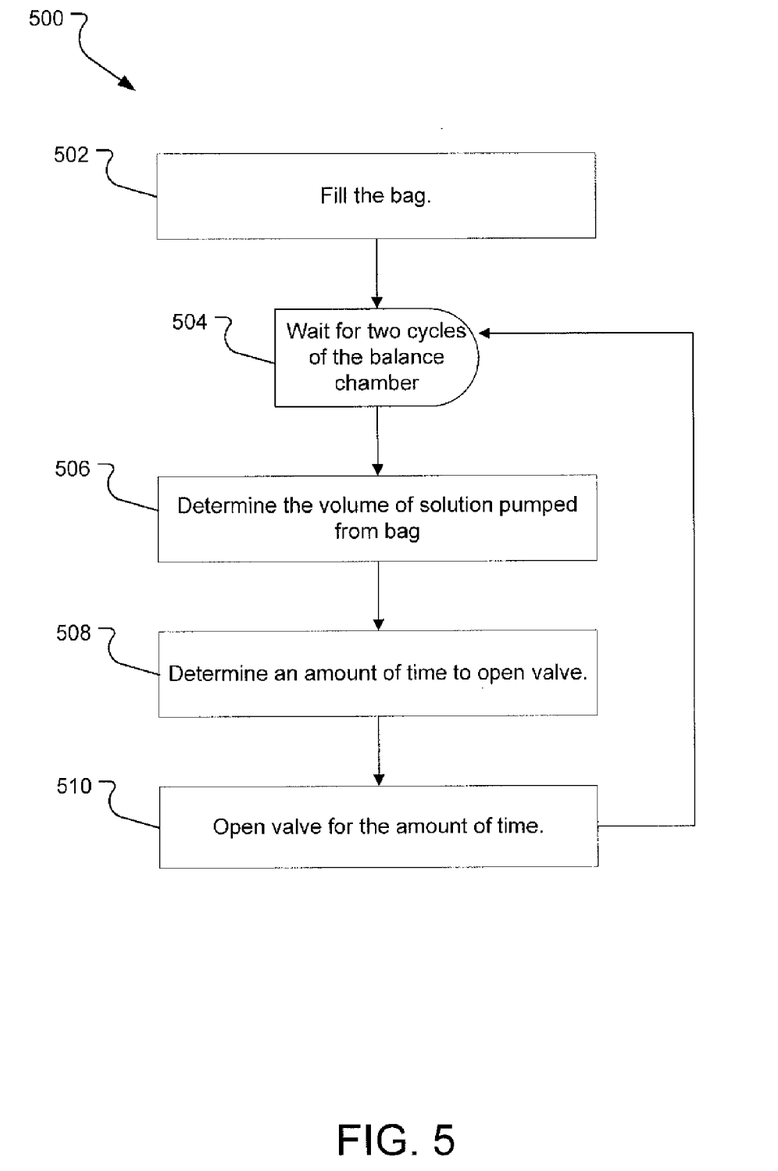
FIG. 5 is a flow chart depicting a method of early detection of a low sodium bicarbonate level in a solution flowing from the collapsible bag of the hemodialysis system of FIG. 1.

FIG. 5 is a flow chart illustrating a method of increasing the dissolution of sodium bicarbonate into the solution in the bag 82. Referring to FIG. 5, the controller performs an initial fill of the bag 82. The initial fill of the bag includes opening the valve 54 to allow liquid to enter the bag. As the liquid saturates the sodium bicarbonate, the pressure in the bag, as measured by the pressure sensor 117 increases. The fill process ends when the requisite pressure of 90 mmg is obtained.

The controller waits for two cycles of the balance chamber (504). During this period, signals are received from the bicarbonate pump 113 indicating the volume of bicarbonate solution that has been pumped from the bag 82.

The controller sums the volume of bicarbonate solution pumped from the bag (506) during each pulse, as reported by the bicarbonate pump 113.

The controller determines an amount of time to open the value (508). The duration is determined in order to add the same volume of liquid to the bag 82 as was removed from the bag 82. The controller compares the volume of solution pumped to the characteristics of the valve 54 to determine the amount of time to keep the valve 54 open.

The controller opens the valve 54 for the determined amount of time (510). While the valve 54 is open, liquid flows through the subsystem line 56 and into the bag 82.

While the controller is controlling the flow of liquid into the bag 82, the controller is monitoring the pressure sensor 117 and the air separation chamber 102. If the pressure measured by the pressure sensor 117 drops to 20 mmg, the controller opens the valve 54 to allow more liquid to enter the bag. If the controller detects several consecutive ventings of the air separation chamber, the controller opens the valve 54 to add additional liquid to the bag 82.

While the layer of liquid 95 in the bag 82 has been described as being maintained by adding liquid to the bag based on the volume of liquid pumped from the bag, the layer of liquid 95 may alternatively be maintained using other techniques. In certain implementations, the layer of liquid 95 is maintained at a desired depth of thickness (e.g., 0.5 inch to 1.5 inch) by comparing a measure of the pressure in the bag 82, as measured by the pressure sensor 117, to an expected pressure that changes based on the operation of the dialysis machine. For example, after the beginning portion 402 of the operation the expected pressure will gradually decrease as the bag 82 empties during the middle portion 404 and end portion 406 of the operation. The controller may determine a period of time to open the valve 54 based on the difference between the measured pressure and the expected pressure.

The layer of liquid 95 may alternatively be maintained by adding liquid to the bag based on a comparison of the weight in the bag 82, as determined by a scale or other weight sensor (not shown), to an expected weight that changes based on the operation of the dialysis machine. For example, after the beginning portion 402 of the operation the expected weight will gradually decrease as the bag 82 empties during the middle portion 404 and end portion 406 of the operation. The controller may determine a period of time to open the valve 54 based on the difference between the measured weight and the expected weight.

As another example, the layer of liquid 95 may be maintained by an optical sensor (not shown) that determines the depth of the layer of liquid 95 relative to the layer of sodium bicarbonate 93. The controller may add liquid to the bag 82 by opening the valve 54 until the optical sensor determines that the depth of the layer of liquid 95 is within an acceptable range (for example, 0.5 to 1.5 inch deep).

In other implementations, the layer of liquid 95 in the bag 82 is maintained by comparing a number of balance chamber cycles during the operation of the dialysis machine to a table.

While the liquid referenced in this disclosure as being introduced to the bag 82 to form the bicarbonate solution or dialysate will typically be purified water, it is intended that the terms "liquid" and "liquids" will encompass other appropriate liquids for the purposes of the disclosed method and arrangement.

As used in this disclosure, the term "air separation chamber" is used to signify a structure that allows the separation of gases from a solution, and permits the separate removal of each through respective outlets. Further, as used in this disclosure, the term "gas" or "gases" is not limited to air, but may include other gases, such as carbon dioxide, etc.

While the valve 42 illustrated in FIG. 2 has been described as being used to control flow to the mainline segment 20a, the pressure regulator 40 may alternately or additionally control the pressure of the fluid (and thus the flow of the fluid) as it passes through the section of the mainline segment 20a.

While the bag 82 has been described as a flexible bag, any other appropriate structure may alternatively be used. For example, a rigid container, a semiflexible container, or a flexible container can be used.

While the bag 82 has been described as containing powdered sodium bicarbonate concentrate to form sodium bicarbonate solution, any of various other solid concentrates (e.g., powdered concentrates) can alternatively be used to form different types of solutions. In some implementations, for example, other types of salts can be provided in the bag. Examples of other types of solid concentrates that can be used include sodium actetate concentrate.

While the venting structure 43 is described to be included in the third chamber 24c of the hydrochamber 24, other venting structures can be included in other chambers.

While only one controller is described, multiple controllers may alternatively be used.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a display device (e.g., the display device of the dialysis machine 12), for example, a CRT (cathode ray tube) or LCD (liquid crystal display) monitor, for displaying information to the user and a keyboard or keypad and/or a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method performed by a data processing apparatus, the method comprising:
   receiving, at the data processing apparatus, an indicator related to a thickness of a layer of a solution adjacent to a dissolvable solid concentrate in a container, the indicator including a first measure of a conductivity of a liquid supplied to the container to form the solution and a second measure of a conductivity of the solution leaving an air separation chamber fluidly coupled to the container; and
   causing, based at least in part on the received indicator, a valve to release more of the liquid supplied to the container and thereby cause a quantity of the liquid to fall freely onto a surface of the layer of the solution to maintain the layer of solution adjacent to the solid concentrate at a depth that is kept within a particular depth range over time, wherein the depth allows liquid introduced into the container to agitate the solution adjacent to the solid concentrate to cause mixing of the solid concentrate with the solution.

2. The method of claim 1, wherein the solid concentrate is a salt.

3. The method of claim 2, wherein the salt is sodium bicarbonate.

4. The method of claim 1, further comprising:
   obtaining a measurement of a volume of solution pumped from the container by a pump during a first period of time; and
   determining a second period of time based on the measurement;
   wherein maintaining the layer of solution at the depth comprises introducing the liquid by opening a valve that controls the supply of the liquid into the container for the second period of time.

5. The method of claim 4, wherein the first period of time is based on a number of cycles of a balance chamber connected to the pump.

6. The method of claim 4, further comprising pumping the solution to a dialyzer.

7. The method of claim 1, wherein the particular depth range is 0.5 to 1.5 inches.

8. The method of claim 1, further comprising:
   obtaining a measurement of pressure within the container;
   comparing the measurement to an expected pressure; and
   determining a period of time based on the comparison;
   wherein maintaining the layer of solution at the depth comprises introducing the liquid by opening a valve that controls the supply of the liquid into the container for the period of time.

9. The method of claim 1, further comprising:
   obtaining a measurement of the weight of the container;
   comparing the measurement to an expected weight; and
   determining a period of time based on the comparison;

wherein maintaining the layer of solution at the depth comprises introducing the liquid by opening a valve that controls the supply of the liquid into the container for the period of time.

10. The method of claim 1, wherein maintaining the layer of solution at the depth comprises introducing the liquid through an inlet that resides above the layer of solution.

11. The method of claim 10, wherein the introduced liquid falls from the inlet into the layer of solution.

12. The method of claim 1, wherein the layer of solution is kept at a depth that provides enough solution for the solid concentrate to saturate the solution.

13. The method of claim 1, wherein the layer of solution is kept at a depth that prevents the layer of solution from dampening the liquid as it is introduced into the container to a degree that results in agitation of the solution adjacent to the solid concentrate that is insufficient for adequate mixing of the solid concentrate with the solution.

14. The method of claim 1, wherein the layer of solution is kept at a depth that is shallow enough for the liquid introduced into the container to sufficiently agitate the solution adjacent to the solid concentrate.

15. The method of claim 1, wherein the indicator includes a time-based identification of a portion of operation.

16. The method of claim 1, wherein the indicator includes, at least in part, a volume of solution leaving the container.

17. The method of claim 1, wherein the indicator includes, at least in part, an output signal from a depth sensor.

18. The method of claim 17, wherein the depth sensor includes an optical sensor.

19. The method of claim 1, wherein the indicator includes, at least in part, a pressure in the container.

20. The method of claim 1, wherein the indicator includes, at least in part, a number of balance chamber cycles.

21. The method of claim 1, wherein the indicator includes, at least in part, a measurement of a weight of the container.

* * * * *